(12) United States Patent
Hansen

(10) Patent No.: US 6,970,246 B2
(45) Date of Patent: Nov. 29, 2005

(54) METHOD AND APPARATUS FOR DETECTING FLUORESCENCE OF A SAMPLE

(75) Inventor: Frans Ejner Ravn Hansen, Frederiksberg C (DK)

(73) Assignee: ChemoMetec A/S, Allerod (DK)

( * ) Notice: Subject to any disclaimer, the term of this patent is extended or adjusted under 35 U.S.C. 154(b) by 366 days.

(21) Appl. No.: 10/257,271

(22) PCT Filed: Apr. 11, 2001

(86) PCT No.: PCT/DK01/00265

§ 371 (c)(1),
(2), (4) Date: Oct. 10, 2002

(87) PCT Pub. No.: WO01/77648

PCT Pub. Date: Oct. 18, 2001

(65) Prior Publication Data

US 2004/0061070 A1 Apr. 1, 2004

(30) Foreign Application Priority Data

Apr. 11, 2000 (DK) .................... PA 2000 00604

(51) Int. Cl.$^7$ ............................................. G01N 21/64
(52) U.S. Cl. ..................... 356/417; 356/318; 250/458.1
(58) Field of Search ................................. 356/317, 318, 356/417; 250/458.1, 459.1, 461.1, 461.2

(56) References Cited

U.S. PATENT DOCUMENTS

| | | | |
|---|---|---|---|
| 4,311,358 A | 1/1982 | Gibbons et al. | 350/91 |
| 4,421,772 A | 12/1983 | Munck et al. | 426/231 |
| 4,515,445 A | 5/1985 | Müller et al. | 350/524 |
| 4,548,499 A | 10/1985 | Eisert et al. | 356/218 |
| 4,791,310 A | 12/1988 | Honig et al. | 250/458.1 |
| 4,804,845 A | 2/1989 | Takeuchi | 250/367 |
| 5,072,382 A | 12/1991 | Kamentsky | 364/413.08 |
| 5,099,363 A | 3/1992 | Lichtman | 359/900 |
| 5,235,457 A | 8/1993 | Lichtman et al. | 359/368 |
| 5,521,755 A | 5/1996 | Stankewitz | 359/385 |
| 5,752,767 A | 5/1998 | Muchlemann | 362/277 |
| 5,805,342 A | 9/1998 | Gravely | 359/618 |
| 5,832,931 A | 11/1998 | Wachter et al. | 128/898 |
| 5,872,623 A | 2/1999 | Stabile et al. | 356/73 |
| 5,900,949 A | 5/1999 | Sampas | 358/482 |
| 5,917,280 A | 6/1999 | Burrows et al. | 313/506 |
| 5,926,262 A | 7/1999 | Jung et al. | 356/73 |
| 5,943,129 A | 8/1999 | Hoyt et al. | 356/318 |
| 5,962,218 A | 10/1999 | Leland et al. | 435/6 |
| 6,025,601 A | 2/2000 | Trulson et al. | 250/461.2 |
| 6,026,319 A | 2/2000 | Hayashi | 600/476 |
| 6,031,661 A | 2/2000 | Tanaami | 359/368 |

FOREIGN PATENT DOCUMENTS

| | | |
|---|---|---|
| EP | 0 087 574 | 9/1983 |
| WO | 99/37999 | 7/1999 |
| WO | 00/28297 | 5/2000 |

OTHER PUBLICATIONS van del Doel et al., "Fluorescence detection in (sub-)nanoliter microarrays," p. 28–39.

*Primary Examiner*—F. L. Evans
(74) *Attorney, Agent, or Firm*—Jacobson Holman PLLC

(57) ABSTRACT

The present invention relates to an apparatus and a method for detecting the fluorescence of a sample, wherein the apparatus comprises excitation light source located on the same side of the sample as the detecting means. The apparatus may be constructed as a single-sided as well as a double-sided system, wherein the double-sided system comprises double-sided excitation system and/or double-sided detecting system. The double-sided system may also be a combination of fluorescence system and conventional microscopy. The apparatus may be used for analysis of various types of biological material, liquid as well as solid material, and various other types of material suitable being analysed through fluorescence studies.

55 Claims, 4 Drawing Sheets

METHOD AND APPARATUS FOR DETECTING FLUORESCENCE OF A SAMPLE

BACKGROUND OF THE INVENTION

Illumination of a sample in microscopy may in principle be categorised into two different classes:

Transmission microscopes, wherein the light source is located or one side of the sample and a sensor or detector on the other side of the sample to detect light being transmitted through the sample.

Reflection microscopes, wherein the light source is located on the same side of the sample as the sensor or detector to detect light being reflected from the sample. The light from the light source is deflected by a partially transmitting and deflecting surface, such as a beam splitter, eg. a dichroic mirror, to illuminate the sample. The light reflected from the sample is allowed to be transmitted through the surface towards the detection means.

In fluorescence microscopy the light source provides excitation light instead of merely illumination. Since the fluorescence signal which is detected is low in intensity compared to the intensity of the excitation light it is of importance that no excitation light is transmitted directly or unfiltered to the detector.

In U.S. Pat. No. 5,805,342 (Gravely) a fluorescence system of the transmission type as well as of the reflection type is shown, wherein the light source travels or scans the sample in the sample plane. The excitation light is either located on the opposite side of the sample or located so that the light is deflected by a partially transmitting and deflecting surface.

In order to produce more compact fluorescence microscopes having more functionalities the present inventors have invented a fluorescence microscope capable of being constructed in a more compact manner than previously known and therefore useable as a portable fluorescence microscope.

SUMMARY OF THE INVENTION

The present invention relates to an apparatus for detecting the fluorescence of a sample comprising a first excitation light means comprising at least a first light source, said excitation light having a main light path, a sample plane for positioning said sample, detection means comprising at least a first detector for detecting light fluorescence signals from the sample, the axis between the detector means and the sample plane being the detection-sample axis, a processor coupled to receive data from the detector(s), a focusing means for focusing the signals to the detection means, said focusing means having a collection angle, wherein the angle between the excitation main light path of the first light source and the detection-sample axis is in a range between the collection angle/2 and 90°.

Furthermore, the invention relates to a method of assessing a parameter of a sample comprising arranging the sample in a sample plane, exposing a first surface of the sample directly with excitation light from a first light means having at least a first light source, by use of focusing means detecting a fluorescence signal from the first surface of the sample onto a first detection means comprising at least a first detector, processing the detected signal obtaining signal data, correlating the signal data to the parameter to be assessed, and assessing the parameter.

DRAWINGS

DEFINITIONS

Figure 1:
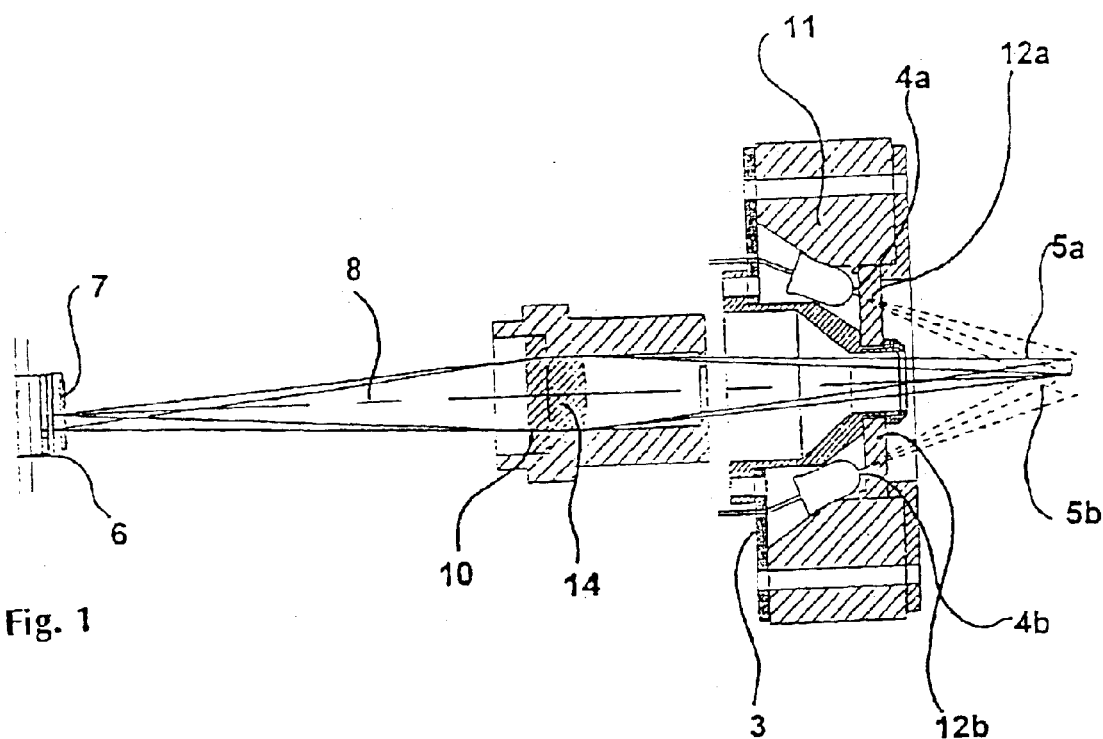
FIG. 1 shows a one sided excitation system.

The following terms have the meanings set forth below:

Collection angle: is used in its conventional meaning, i.e., the angle for which a focusing means can collect signals to be detected by the detection means.

Collection angle/2: means the half of the collection angle.

Detection area: the area of the surface of the sample to be detected by one detection.

Detector-sample axis: the axis from the detector to the sample.

Exposing directly: means that the angle between the main light path and the detection-sample axis is between collection angle/2 and 90°.

Focus depth: the distance an object can move along the axis of a focusing system, without its image is distorted, such distortion being defined as when an image, which when in focus illuminates a single detection element, illuminates an area extending to 2 detection elements in one or two directions, when distorted. When two or more detection elements are combined prior to analysis, the combined detection elements should be considered in the definition of focus depth.

Incidence angle: the angle between the main light path and the detection-sample axis.

Light means: the light system comprising all the light sources for exposing onto one side of the sample.

Light plane: a plane through two or more light sources.

Main light path: the path from the centre of the light beam to the sample plane, which is exemplified by the centre of a light emitting diode.

Sample plane: the plane perpendicular to the detector-sample axis and whereupon the sample is arranged.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The apparatus according to the invention may be a stationary fluorescence microscope or a portable fluorescence microscope. In a preferred embodiment the apparatus is portable for detecting fluorescence of samples in the field.

The light source is arranged in relation to the sample in a manner providing a maximum of the light energy to the sample. Since the light is transmitted from a light source located on the same side of the sample as the detecting means it is possible to increase the intensity of the excitation light above what is practically applicable in transmission fluorescence microscope because the light from the first light source is not transmitted directly into the detection-sample axis.

It is preferred to use a diverging excitation light, such as light emitting diodes for in a cost-effective manner to expose as large area as possible of the sample to the excitation light. The light source may be selected from; a light emitting diode, a laser diode, a laser, a thermal light source (such as a halogen lamp) and a gas discharge lamp, (such as a xenon lamp).

It is often preferred to use more than one light source for the purpose of increasing the flux of light onto the sample, for instance by using two or more light emitting diodes. It is also possible to use more than one light source where some of the light sources have different electromagnetic properties.

The excitation light means preferably comprises at least one light emitting diode (LED), it is however preferred that at least 2 LEDs are provided, more preferred at least 4 LEDs. When using more than one LED, the LEDs are preferably spaced at identical distances from each other. They may be arranged in any symmetrical pattern around the detection-sample axis as long as the light effect is exploited efficiently, such as in a circular pattern, or a square pattern around the detection-sample axis. The excitation lights are preferably arranged in a light plane, ie. a plane through the light sources. The light plane is preferably parallel to the sample plane.

By the use of several LEDs the sample is exposed to excitation light from several angles leading to a substantially optimal excitation of the sample the light source are preferably operated in such a way that all transmit substantially simultaneously. There is no upper limit of the number of LEDs used, but often as many as 30 LEDs are provided, such as up to 20 LEDs.

However for some applications wherein at least a first and a second light sources are arranged in the first excitation light means, the first light source having a different wavelength band than the second light source, the light sources may transmit in an alternating manner. By the use of two different light sources it is possible to obtain two different fluorescence signals from the sample. Thereby it is possible to obtain at least two different kinds of information because when light sources of one wavelength are transmitting one type of signal is transmitted to the detector and when light sources of another wavelength is transmitting another type of signal is transmitted to the detector.

If a less diverging light source is used a diverging optical means may be arranged in the excitation light path to diverge the excitation light properly. Independent of how the light source(s) are diverging it is preferred that the light is emitted directed onto the sample without being deflected from its light path in order to ensure proper excitation of the sample as well as reducing the risk of having excitation light being transmitted directly to the detection means.

When using laser diodes as the excitation light the proper divergence may be accomplished by an arrangement of at least 4 laser diodes optionally provided with diverging means.

The light source may provide light of any suitable wavelength, such as in the range between 200 to 980 nm, such as in the range of 200–700, 200–600, 200–500 or 200–400.

In another embodiment the light source is arranged in a first light plane parallel to the sample light plane, said first light plane being positioned at a distance from the sample plane behind the detector. By this construction the light is either emitted from the light sources directly towards the sample plane travelling around the detector means. In another embodiment the light is initially directed in the opposite direction towards a reflector reflecting the light beams towards the sample plane travelling around the detector means. Independent of the positioning of the excitation light it has to be ensured that the angle between the excitation main light path and the detection-sample axis is as defined above. The reflector may be any suitable reflecting means, such as a concave mirror.

The detection means is preferably arranged in a housing where the light sources are located behind the detection means. In this case the housing is provided with an opening allowing the signals emitted from the sample to reach the detectors.

In one embodiment of the invention the light sources are arranged so that the first excitation light means is located in a first light plane parallel to the sample plane, said first plane being between the sample plane and the first detection means. The incident angles of at least the first light source of the first excitation light means is between the collection angle/2 and 90°. Preferably all the light sources have incidence angles in this range, more preferably all light sources have substantially identical incidence angles.

Thereby it is ensured that the excitation light path and the emitted signals do not interfere, resulting in errors in the signals to be detected.

The incident angle is preferably in the range between 30° and 90°, more preferably between 45° and 85°, such as between 50° and 85°, such as between 50° and 75°, such as between 50° and 60° to provide a suitable excitation of the sample.

The excitation light is transmitted directly to the sample, i.e. without being deflected by a beam splitter, mechanically by for example baffles, or the like whereby it is possible to construct the apparatus more compact and having fewer parts since no deflection means has to be incorporated into the light paths.

In order to further avoid signal errors, the light source is enclosed or otherwise shielded to ensure that no excitation light is transmitted directly to the detecting means.

The sample plane is constituted by the surface of the sample. In one embodiment of the apparatus means for positioning the sample in the sample plane are arranged. For example a plate having a recess may be located in the sample plane for receiving the sample to be assessed. In particular for liquid samples, the sample plane may comprise a sample compartment for housing the sample at least during detection. The sample compartment may be a stationery compartment or a replaceable compartment, such as a cassette shaped to fit into the sample plane.

A sample compartment, containing the sample being analysed, arranges preferably as much sample volume as possible in such a way that it can be exposed to the array of detection elements, thus allowing the analysis of a large area of the sample simultaneously. One method for accomplishing this, is to define the thickness of sample compartment in a direction which is not parallel to the plane of detection elements, thus increasing the effective volume per area of sample compartment exposed to the detection elements. The optimum thickness often being determined by any effective focus depth of a focusing system.

In such cases the sample compartment limits the dimension of the sample in the direction which is substantially not parallel to the plane of array of detection elements, to a thickness of at least 20 $\mu$m or less, preferably to a thickness of more than 20 $\mu$m, more preferably to a thickness of more than 40 $\mu$m, more preferably to a thickness of more than 60 $\mu$m, more preferably to a thickness of more than 80 $\mu$m, more preferably to a thickness of more than 100 $\mu$m, more preferably to a thickness of more than 140 $\mu$m, more preferably to a thickness of more than 180 $\mu$m, more preferably to a thickness of more than 250 $\mu$m, more preferably to a thickness of more than 500 $\mu$m, more preferably to a thickness of more than 1000 $\mu$m.

Similarly, it is advantageous to extend the detection area of the sample compartment in a direction parallel to the array of detection elements, thus increasing the effective area of the sample being exposed to the array of detection elements. For some of these applications, the length of the dimension being 1 mm or more, preferably 2 mm or more, more preferably 4 mm or more, more preferably 10 mm or more, more preferably 20 mm or more, more preferably 40 mm or more, more preferably 100 mm or more, more preferably 200 mm or more, more preferably 400 mm or more.

For some applications a tubular sample compartment is used whereby it also is possible to increase the area of sample being analysed simultaneously by increasing the radius of such tubular sample compartment. The optimum radius of such sample compartment is often determined by the arrangement of the various components of the system, such as focus depth. The tube can in these circumstances have an inner radius of more than 0.01 mm, preferably 0.02 mm or more, more preferably 0.04 mm or more, more preferably 0.1 mm or more, more preferably 0.2 mm or more, more preferably 0.4 mm or more, more preferably 1 mm or more, more preferably 2 mm or more, more preferably 4 mm or more, more preferably 10 mm or more.

The sample compartment may be a disposable sampling device as described in PCT/DK99/00605 which is hereby incorporated by reference.

The apparatus according to the present invention allows the assessment of samples of a wide variety of volumes. The volume of the sample from which signals are exposed onto the array is normally in the range between 0.01 $\mu$l and 20 $\mu$l, such as in the range between 0.01 $\mu$l and 10 $\mu$l, such as in the range between 0.01 $\mu$l and 4 $\mu$l, such as in the range between 0.02 $\mu$l and 10 $\mu$l, preferably in the range between 0.04 $\mu$l and 2 $\mu$l, such as in the range between 0.05 $\mu$l and 2 $\mu$l, such as in the range between 0.01 $\mu$l and 1.50 $\mu$l.

The focus depth of the system is often important for the determination of optimal dimensions of a sample compartment. It has been found that it is possible to use dimension which exceeded the focus depth of a focusing system, even to an extend where the dimension was greater than 1 times and less than 1.5 times the focusing depth, more preferably equal to, or greater than 1.5 times and less than 2 times said focusing depth, more preferably equal to, or greater than 2 times and less than 3 times said focusing depth, more preferably equal to, or greater than 3 times and less than 4 times said focusing depth, more preferably equal to, or greater than 4 times and less than 6 times said focusing depth, more preferably equal to, or greater than 6 times said focusing depth.

The sample is preferably at stand still during the exposure to obtain stand still conditions for the detection means.

Filters

In order to obtain the fluorescent signal required for detection a filter is interposed in the light path between the light source and the sample. The filter may be any suitable filter for the excitation light/emission light. The filter may be selected from interference filters, coloured filters, and polarisation filters. Preferably a separate filter is provided for each light source. The filters may be substantially identical, but for some samples it may be convenient to use different filters.

For example, a monochromatic device can be used to separate electromagnetic radiation into one or more wavelength components before one or several of these wavelength components are transmitted onto the sample either one at a time or more than one at a time, preferably when more than one wavelength component is transmitted onto the sample simultaneously the wavelength components are transmitted onto different portions of the sample thus giving an opportunity to obtain qualitative as well as quantitative information about particles in the sample. This is in particular of interest when the sample contains particles which respond differently to different wavelength components.

It is preferred that the filters for the individual light sources in an excitation light means are connected, e.g. are arranged on a continuous supporting material. Thereby the construction of the microscope is facilitated since the connected filters may be positioned in the apparatus in one handling operation.

The supporting material may be any suitable material either being non-transparent to the excitation light or having filter function corresponding to the filters used.

The shape of the supporting material preferably corresponds to the pattern of the light source arrangement, such as semi-circular, circular, rectangular, triangular, square-formed. When the light are arranged around the detection sample axis it is important that the signals emitted from the sample are allowed to pass to the detection means.

In a preferred embodiment the filter is circular having a circular "hole", the diameter of said "hole" preferably corresponding to or being larger than the diameter of the signal beam.

It is envisaged by the present invention that the filters may be changeable, so that a variety of wavelength components may be transmitted to the sample. In this embodiment the filter(s) as such may be changed, or the filter and light sources are changed. In the latter situation the are filter(s) and light sources are preferably combined as a replaceable filter-light unit.

Light which is transmitted onto the sample can be focused by a focusing system, comprising one or more lenses. The effect of such a focusing system is often to increase the effective efficiency of the light source.

Furthermore, a monochromatic device can be used to separate the electromagnetic signals emitted from, or transmitted through the sample into one or more wavelength components before such electromagnetic signals are detected by a detection element, either in such a way that one wavelength is measured at a time or in such a way that more than one wavelength components are measured at a time. This is in particular of interest when the sample contains particles which respond differently to different wavelength components for instance when a particle is capable of emitting photoluminescence with different properties dependent on the nature of the particle. This effect can also be produced by the use of more than one type of light source which have different wavelength characteristics, preferably in combination with a monochromatic device.

In particular spectrally rich electromagnetic radiation emitted from or transmitted through the sample may be spatially separated into a plurality of wavelength components, in such a way that each of the detection elements in the array of detection elements, measuring information from substantially the same fraction of the sample, is exposed to substantially different wavelength components.

This may be accomplished by using one or several of the following, but not limited to: interference filters, coloured filters, an optical grating, a prism, an optically active crystals.

Furthermore, the excitation light or fluorescence signals may be intensity modulated, such as by optically active crystals or interferometry, preferably by the use of a Michelson interferometer, more preferably by the use of an interferometer where at least one reflecting surface can be moved.

It is often preferable to use one or several state of the art image processing techniques, such as 2 dimensional filtering or image identification, to assess the number of particles in a sample, or any morphological property of a particle.

The detection means may comprise any defectors capable of sensing or detecting the fluorescence signal emitted from the sample.

In a preferred embodiment detection means comprises a detector being an array of detecting devices or detection elements, such as a charge coupled device (CCD) the CCD may be a full frame CCD, frame transfer CCD, interline transfer CCD, line scan CCD, an eg. wavelength intensified CCD array, a focal plane array, a photodiode array or a photodetector array, such as a CMOS. The CMOS is preferably a CMOS image sensor with on-chip integrated signal condition and/or signal processing. Independent of the choices of any of the above detection devises the detection means may further comprise a white/black or colour CCD or CMOS.

The size of the detection elements determines to some extend its sensitivity. In some applications it is therefore of interest to have detection elements of size of about 1 $\mu m^2$ or less. In certain situations the size of the detection elements in the array of detection elements is less than 20 $\mu m^2$, preferably less than 10 $\mu m^2$, more preferably less than 5 $\mu m^2$, more preferably, less than 2 $\mu m^2$, more preferably less than or equal to 1 $\mu m^2$. In other situations the size of the detection elements in the array of detection elements is greater than or equal to 5000 $\mu m^2$, such as greater than or equal to 2000 $\mu m^2$, more preferably greater than or equal to 1000 $\mu m^2$, such as greater than or equal to 500 $\mu m^2$, or even greater than or equal to 200 $\mu m^2$, more preferably greater than or equal to 100 and less than 200 $\mu m^2$, more preferably greater than or equal to 50 and less than 100 $\mu m^2$, more preferably greater than or equal to 20 and less than 50 $\mu m^2$.

The array of detection elements is preferably sensitive to electromagnetic radiation of wavelength in one or several of the following region: 100 nm to 200 nm, 200 nm to 600 nm, 300 nm to 700 nm, 400 nm to 800 nm, 600 nm to 1 $\mu m$, 800 nm to 2 $\mu m$, 2 $\mu m$ to 10 $\mu m$, 5 $\mu m$ to 10 $\mu m$, 10 $\mu m$ to 20 $\mu m$, 20 $\mu m$ to 40 $\mu m$.

The inclusion of a focusing device for the focusing of a signal from the sample onto the detection elements in such a manner as to maximise the collection angle, the collection angle being defined as the full plane angle within which a signal is detected, has in many situations been found to give improved conditions for an assessment. Surprisingly it was found that such a wide collection angle, even to the extent that the objective used in the focusing distorted the aspect ratio of the image of any particle differently across the plane in which the detection elements were placed, or produced variation in the focusing across the sample being analysed, or reduction of the focusing quality, could be used in the assessment of for example the number of particles in the sample.

The aspect ratio of the detection elements can be important in the collection of signals for the assessment of particles. A ratio of about 1/1 is some times preferred but under some conditions it can be preferred to use ratio different from 1/1. In particular when this facilitates detection of signals from increased volume of any sample, thus allowing simultaneous assessment of for examples more particles. In those circumstances the ratio of the shorter of the height or the width, to the longer, of the height or the width of the detection elements in the array of detection elements is substantially equal or less than 1, preferably less than 1/2 more preferably less than 1/4, more preferably less than 1/10, more preferably less than 1/50, more preferably less than 1/100, more preferably less than 1/200.

Another way of expressing the ratio at which the image should preferably be formed on the array is to consider the imaging of an individual particle of the sample on the detection elements. It is often preferred that the individual particles are imaged on at the most 100 detection elements, such as at the most 81 detection elements, such as at the most 64 detection elements, such as at the most 49 detection elements, such as at the most 36 detection elements, such as at the most 25 detection elements, in particular on at the most 16 detection elements and more preferred at the most 9 detection elements. It is even more preferred that individual particles the parameter or parameters of which is/are to be assessed are imaged on at the most 5 detection elements, or even on at the most 1 detection elements. The larger number of elements per particle will provide more information on the individual particles, while the smaller number of elements per particle will increase the total count that can be made in one detection exposure.

Signals from at least a portion of the sample are focused onto the array of detection elements, by the use of a focusing means, preferably by the use of one lens, it is however possible to use two lenses, or more than two lenses. The number of lenses used for the focusing system can affect the complexity of any measuring system.

The focusing of a signal from the sample onto any detector is dependent on the position of the sample relative to any detector. When the construction of measuring system is such, that the relative position of the sample and any detector can vary, then there is advantage in being able to adjust the focusing of the system. This can often be achieved by first taking at least one measurement of any signal from the sample and then on the bases of this, to adjust the focusing of the system. This procedure can be repeated a number of times in order to obtain acceptable focusing. In the same manner the focusing of signal from the sample or sample material is adjusted, preferably where the extend of the adjustment is determined by at least one measurement of a signal from the sample.

The collection angle of a focusing arrangement used can have effect on the intensity of any signal collected on the array of detection elements. When high sensitivity is needed it is therefore practical to increase the collection angle. The preferred size of the collection angle can also be determined by other requirements which are made to the system, such as focusing depth. In these situations the collection angle of the focusing means is preferably at least 2 degrees, preferably more than 5 degrees, more preferably more then 15 degrees, more preferably more than 20 degrees, more preferably more than 50 degrees, more preferably more than 120 degrees, more preferably more than 150 degrees.

The signal which is detected is substantially caused by one or several of the following: photoluminescence with lifetime of the exited state of less than or equal to $10^{-6}$ seconds, photoluminescence with lifetime of the exited state of garter than $10^{-6}$ seconds, chemiluminescence, rayleigh scatter, raman scatter, attenuation of electromagnetic radiation, absorption of the electromagnetic radiation, scatter of the electromagnetic radiation.

The signals measured from one or more detection elements may be corrected for systematic or varying bias by the use of a calculating means, the bias correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

The bias correction may be performed by subtracting the results obtained in one or several of other measurements from the measured signal, preferably where the other measurements are one or several of measurements of the same sample, or sample material, more preferably where the other measurement is the measurement taken previously of the same sample or sample material.

Also the signal from one or more detection elements may be corrected for intensity by the use of a calculating means, said correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

In some situations e.g. in an analogue-to-digital conversion it could also be of interest to adjust the level of 2, preferably 3, more preferably 4, more preferably 5, more preferably 6, more preferably 7, more preferably 8, more preferably more than 8, separate output channels in such a way that one, preferably more than one, of the output channels has/have substantially different level from the other output channel(s), where the identification of which of the output channels, or combination thereof, has substantially different output level, is correlated to the intensity of said signal.

For the analysis of any measured signal it is often necessary to digitalise the signal, in such a way that a given intensity of any signal is transformed into a digital representation. This can be done by having a series of channels, were the information about which of these channels has signal which differs from the other channels determines the intensity, or even by having more than one of this channels forming a combination, preferably in a way similar to binary representation.

Information of the signals detected by the detection means are input into a processor for processing, displaying and optionally storing the information The signal information may be displayed on a display connected to then processor and/or printed. The information displayed may be any kind of information relating to the signals measured and/or the system used, such as a number, size distribution, morphology, classification of particles, excitation wavelength, emission wavelength, magnification.

Storage capacity, for instance used for storing information about measured signals from the detection elements, is often one of those components which have considerable effect on the cost of production. It is therefore of interest to be able to perform the assessment of parameters without substantial any use of such storage capacity, such that the assessment of biological particles in a sample is performed without the use of substantially any storage capacity means being used to store measured signals from the detection elements in the array of detection elements.

On the other hand, it is often difficult to accomplish assessment without the use of any storage capacity, but preferably the amount of such storage capacity should not be more than what is needed to store the information from all measured detection elements, preferably where only a fraction of the information can be stored.

In some situations measured signal from the detection elements in the array of detection elements is stored by means of storage capacity, the storage capacity being able to store a number of measurements equivalent to, or less than, the number of detection elements, preferably less than 1/2 the number of detection elements, more preferably less than 1/4 the number of detection elements, more preferably less than 1/8 the number of detection elements, more preferably less than 1/16 the number of detection elements, more preferably less than 1/32 the number of detection elements, more preferably less than 1/64 the number of detection elements, more preferably less than 1/128 the number of detection elements, more preferably less than 1/256 the number of detection elements, more preferably less than 1/512 the number of detection elements, more preferably less than 1/1024 the number of detection elements in the array of detection elements.

In other certain circumstances it is advantageous that the measured signal from the detection elements in the array of detection elements is stored by means of storage capacity, the storage capacity being able to store a number of measurements greater than the number of detection elements, preferably equivalent to, or greater than, 2 times the number of detection elements, more preferably equivalent to, or greater than, 4 times the number of detection elements, more preferably equivalent to, or greater than, 8 times the number of detection elements, more preferably equivalent to, or greater than, 16 times the number of detection elements, more preferably equivalent to, or greater than, 32 times the number of detection elements, more preferably equivalent to, or greater than, 64 times the number of detection elements, more preferably equivalent to, or greater than, 128 times the number of detection elements, more preferably equivalent to, or greater than, 256 times the number of detection elements, more preferably equivalent to, or greater than, 512 times the number of detection elements, more preferably equivalent to, or greater than, 1024 times the number of detection elements in the array of detection elements.

Other, more complicated aspects of the assessment of parameters, can require the use of considerable amount of storage capacity. In this aspect it can therefore be necessary to have storage capacity which can store more information than is collected in one measurement of the detection elements used.

It is possible to make the correlation and the assessment of the parameters of the sample by using a calculation mean, preferably a digital computer, one commercially available from Analogue Devices (ADSP 2101), equipped with storage capacity which can only store information in amount substantially equivalent to a small fraction of the total number of detection elements, the assessment of the number of objects then being based on substantially real time processing of data, preferably in such a way that the measured information from each detection element, or a line of detection elements, or two or more lines of detection elements, is used for the assessment, substantially without any delay, such as a delay which would otherwise be caused by storing the measured information.

However, it is often preferred to store substantially all measured information by the use of a first calculation mean, preferably a digital computer, before the processing of the information by a second calculation mean, preferably a digital computer, and thus allowing the measured information to be processed at substantially the same rate it is obtained, but with a substantial time delay between the measurement of any information and the processing of the same information; preferably, this is accomplished by using only one calculating mean, preferably a digital computer, equipped with enough resources to accomplish the task.

The apparatus is particular useful for assessing parameters of a sample at a low magnification or enlargement. Thereby it is possible to achieve information relating to a large area of the sample.

The magnification may be provided by the focusing means. The magnification of such focusing can be different from 1/1, depending on the set-up of other components of the system, or the particles or sample material used. For instance can enlargement be practical when assessing morphological properties of a particle.

In situations where the particles are relatively small the ratio of the size of a biological particle, to the size of the image of the biological particle on the array of detection elements could be 1/1 or less, preferably less than 1/1 and higher than 1/100, and even less than 1/1 and higher than 1/40, or in other preferred situations less than 1/1 and higher than 1/10, and event in some situations it is preferred the ratio being less than 1/1 and higher than 1/4, more preferably less than 1/1 and higher than 1/2.

When the particles in question have dimensions which are comparable to the size of a detection element, it is often preferred to have magnification of about 1/1, thus focusing the image of any particle on any one or just few detection elements. This can under some condition give favourable detection of any signal.

In these situations it is preferred that the ratio of the size of a biological particle, to the size of the image of the biological particle on the array of detection elements is in the interval between 5/10 and 20/10, preferably in the internal between 6/10 and 18/10, more preferably in the interval between 7/10 and 16/10, more preferably in the interval between 8/10 and 14/10, more preferably in the interval between 9/10 and 12/10, more preferably substantially equal to 10/10.

When analysing particles which have dimensions which are comparable to, or bigger than the detection elements used, it is often advantageous to reduce the size of the image of such particle, to a degree where the size of the image is comparable to the size of a detection element.

In these situations it is preferred that the ratio of the size of a biological particle, to the size of the image of the biological particle on the array of detection elements is 1/1 or less, preferably less than 1/1 and higher than 1/100, more preferably less than 1/1 and higher than 1/40, more preferably less than 1/1 and higher than 1/10, more preferably less than 1/1 and higher than 1/4, more preferably less than 1/1 and higher than 1/2.

Thus, it is often preferred that the spatial representation exposed onto the array of detection elements is subject to such a linear enlargement that the ratio of the image of a linear dimension on the array of detection elements to the original linear dimension in the exposing domain is smaller than 40:1, normally at the most 20:1, preferably smaller than 10:1 and in many cases even at the most 6:1 or even smaller than 4:1.

The enlargement is suitably correlated to he parameters to be determined, in particular to the size of the particles for which a parameter is to be assessed. The size of the particle is given by approximating the particle to a round particle, wherein the size mentioned below relates to the diameter of the particle. Preferably the smallest dimension of the particle is used as the diameter when approximating the particle to a round particle. Thus, for example, when the size is between 0.1 $\mu$m to 5 $\mu$m, such as between 1/3 $\mu$m to 3 $\mu$m, the above-mentioned ratio is preferably in the range between 40:1 and 1:10, more preferably in the range between 20:1 and 1:10, such as in the range between 10:1 and 1:10. In most embodiments which have proved to give excellent results in practice, the ratio is in the range between 6:1 and 2:1.

When the size is between 1 $\mu$m and 100 $\mu$m, such as between 3 $\mu$m and 100 $\mu$m, such as between 5 $\mu$m and 100 $\mu$m, the above-mentioned ratio is normally in the range between 3:1 and 1:100, preferably in the range between 2:1 and 1:100. In many practical embodiments, the ratio will be in the range between 2:1 and 1:2. It can be interesting, in particular with small high precision detection elements, to work with very small rations, such as in the range between 1.4:1 and 1:100, e.g., in the range between 1:1 and 1:100.

Surprisingly it was found that the aspect ratio of an image can be considerably distorted on the array of detection elements, without that having considerable negative effect on the assessment of particles. In such a situation it preferred that the ratio of the shorter to the longer of the two dimensions of the image of a biological particle on the array of detection elements is substantially 1 or less, preferably 1/2 or less, more preferably 1/4 or less, more preferably 1/10 or less, more preferably 1/50 or less, more preferably 1/100 or less, more preferably 1/200 or less, relative to the ratio of the corresponding dimensions of the biological particle. In such situation the ratio of the shorter to the longer of the two dimensions of the image of a biological particle on the array of detection elements is in certain circumstances substantially not the same within the area spanned by the array of detection elements.

The apparatus according to the present invention may be used as a one-sided apparatus, i.e. an apparatus for which the excitation light is directed to the sample from the same side of the sample as the side for which the signals emitted from the sample are detected.

By this apparatus a variety of advantages have been achieved as compared to conventional fluorescence microscopes. First of all it is possible to arrange the sample to be assessed directly in the sample plane instead of sliding it into the sample plane between the detector and the excitation light. Furthermore it has become possible to detect surface fluorescence of a sample not being transparent.

As mentioned above it is also possible to increase the intensity of the excitation light without compromising the detectors.

Also samples having a nature whereby it is normally not possible to arrange the sample in a microscope may be assessed by the use of the present system, in that the microscope may be placed directly on the sample whereby the surface of the sample simply constitutes the sample plane.

Finally it is possible to produce a more compact and thereby more easily handled apparatus, in that the excitation light means is arranged on the same side of the sample plane as the detector, thus shortening the axis of the apparatus by at least 25% as compared to conventional apparatuses.

By the present invention it is possible to assess parameters of a sample which has up to now only been reliably assessed by the use of flow cytometric equipment. It is possible to assess parameters of a large sample in one exposure thus reducing the statistical errors normally counted for when assessing large samples by assessing only parts thereof per exposure.

Furthermore, it is possible to obtain more than one fluorescence signal from the sample in one exposure thereby facilitating classification of particles of the sample, due to their different fluorescence signals.

Thus, the one-sided apparatus according to the invention may be constructed in a wide variety of combination, which are all within the scope of this invention. In particular the principal combination discussed below are envisaged.

The apparatus may be constructed as a single fluorescence apparatus wherein the light sources and the excitation light filters are identical.

A multiple fluorescence apparatus, such as an apparatus providing at least two different fluorescence signals, may be provided by at least one of the following:

A first and a second light source, said light sources emitting light in different wavelengths A first and a second filter being different whereby the excitation light of at least two different wavelength are exposed to the sample A first and a second emission filter being different, such as a dual band filter, whereby at least two different fluorescence signals are emitted to the detector(s)

It is however a further advantage that the present apparatus may be constructed as, a double-sided apparatus, whereby excitation light may be directed onto the sample from both sides of the samples, or detection means are arranged to detect signals from both sides of the samples, or a combination of both.

Thus by a double-sided apparatus is meant an apparatus according to the invention further provided with:

A second excitation light means located in a second light plane, said second light plane being parallel with the sample plane and located on the other side of the sample plane as opposed to the first light plane. Thereby the samples is receiving excitation light from both sides of the sample considerably increasing the energy exposed to the sample, and/or A second detection means arranged so that the sample is positioned between the first detection means and the second detection means. Hereby it is possible to assess different information regarding the signals from the sample by one exposure detection. For example the first detection means may be adapted to register the number of particles of the sample, whereas the second detection means is adapted to register the morphology of the particles in the sample.

In a preferred embodiment the double-sided apparatus comprises both double-sided excitation system and double-sided detection system.

The second excitation light means may be any of the light means discussed in relation to the first light means. Depending on the purpose of the fluorescence microscope the light means may be different or identical.

Furthermore, it may be of interest that the excitation light would constitute different wavelength bands whereby illumination with different wavelengths is achieved. The second detection means may be any of the detection means discussed in relation to the first detection means.

The following table 1 shows a non-exhaustive list of combinations of the system configurations according to the present invention.

TABLE 1

System Configurations

| Detector 1 | Emission filter 1 | Excitation 1 | Excitation filter 1 | S | Excitation filter 2 | Excitation 2 | Emission filter 2 | Detector 2 | Configuration No. |
|---|---|---|---|---|---|---|---|---|---|
| X | x | X | x | | | | | | 1 |
| X | x | x/y | x/y | | | | | | 2 |
| X | x | x | x | | x | x | | | 3 |
| X | x | x | x | | y | y | | | 4 |
| X | x | x | x | | | | x | y | 5 |
| X | x | x | x | | x | x | x | y | 6 |
| X | x | x | x | | y | y | y | y | 7 |
| X | x | X | x | | x | x | y | y | 8 |
| X | x | x | x | | | | | x | 9 |
| X | x | x | x | | x | x | | x | 10 |

X denotes one type of detector, emission filter, excitation source, and excitation filter respectively, and Y denotes another type of detector, emission filter, excitation source, and excitation filter respectively.

Configurations Nos: 1 and 2 correspond to a single-sided system, wherein in Conf. 2 two different excitation light sources and/or filters are applied.

Configurations Nos: 3 and 4 correspond to a double-sided excitation system, either for increasing the amount of excitation light (conf. 3) or for adding another type of excitation light (conf. 4)

Configuration Nos: 5 and 6 is a double-sided detection system, wherein the two detectors are different, such as for example having different magnification. Config. No: 6 furthermore uses double excitation.

Configuration No. 7 is a double-sided system with respect to excitation as well as detection. All parameters, ie. detector, emission filter, excitation source, and excitation filter respective are different for the two sides, offering the possibility of obtaining a wide variety of information from the sample.

Configuration No. 8 is also a double-sided system with respect to excitation as well as detection. As opposed to the Config. No. 7 only the detectors and the emission filters are different for the two sides, again offering the possibility of obtaining a variety of information from the sample.

Configuration Nos. 9 and 10 both employ a microscope as the second detector. In Configuration No. 10 the system is double-sided with respect to the excitation sources. The microscope may be any kind of microscope, such as a conventional microscope.

As shown above any suitable combination of light sources, filters, magnification and detectors are envisaged by the present invention, also combinations not expressly shown in this application. In the following preferred embodiments of the two-sided system is discussed.

The apparatus may be a single fluorescence system, wherein excitation light of substantially identical wavelength are exposed to the sample from two sides. Thereby the excitation light may be intensified.

In a double-sided excitation light apparatus a first excitation light means exposes the sample to one wavelength from one side of the sample, and the second excitation light exposes the sample to another wavelength from the other side of the sample. It is understood herein, that of course the first excitation light and the second excitation light respectively, may comprise different light source and/or filters, whereby the sample may be illuminated with even more wavelengths as discussed above.

The double-sided excitation light apparatus may comprise one detector, whereby the apparatus functions as a partly transmitting system.

In another embodiment the double-sided excitation light apparatus comprises two detecting means. Thereby an increased amount of information may be obtained from the sample. In one aspect the two detecting means may obtain equal, although mirror images (the images on the two detectors are mirror images of each other), information relating to the sample providing a validation of the information.

The apparatus according to the invention may also be a double-sided detection apparatus using a one-sided excitation light means. Thereby one detector detects signals being transmitted through the sample.

Independent of the arrangement of excitation light, a double-sided detecting system is capable of increasing the amount of information received. For example different wavelength may be received by the two detectors, and or different detectors, having different sensibility may be used. Furthermore, by using for example different magnification for the two detectors the information relating to the sample may be increased. One side of the system may assess for example number of particles in a large area of the sample, for example by a low magnification, and the other side of the system may assess the morphology of the particles by using a larger magnification. Combinations of magnification may for example be 1:1 and 1:4, 1:1 and 1:10, 1:2 and 1:4, 1:2 and 1:10. The signal information transferred from the two detectors is preferably transmitted to the same processor, whereby the information may be displayed separately, as well as being combined providing for example specific morphology information related to specific particles the position and number of which are detected by the other detector.

It is also possible to use the apparatus according to the invention as a double-sided apparatus where the other side is a conventional light microscope or any other type of microscope. When using the other side of the system as a non-fluorescence microscope, the illumination light for the microscope may be suitably arranged on either side of the sample in relation to the microscope.

The double-sided apparatus comprising a conventional microscope on one side, may comprises a one-sided or a double-sided excitation light system for the fluorescence part of the system.

When using a double-sided detection system the processor of the first detection means may receive signal data from the second detection means as well in order to simplify the apparatus. It is however possible to install a separate processor for each detection means.

The source of electrical power to the apparatus may be a transformer, capable of transforming alternating electrical source with alternating voltage between −150 and 150 volt, or with alternating voltage between −250 and 350 volt, or with alternating voltage between −350 and 350 volt, into substantially direct current voltage.

The invention furthermore relates to a method of assessing a fluorescence signal from a sample, wherein the sample is arranged in the sample plane of the apparatus as discussed above.

According to the method a first surface of the sample is exposed directly to the excitation light from a first light means having at least a first light source, and fluorescence signals from the first surface are focused onto the detector(s) by use of a focusing means and detected by the detector(s). The detected signals are processed whereby signal data are obtained. These signal data may then be correlated to the parameter to be assessed, and finally the parameter(s) of the sample is assessed.

The sample may be any sample from which it is suitable to detect fluorescence signal(s). In many applications the sample is a liquid sample, the content of which is to be assessed. Often the fluorescence signal is related to a parameter of a particle in the sample, such as the number of particles in the sample and/or the morphology of particles in the sample. In particular in this case it is advantageous to apply the method in a double-sided apparatus according to the invention whereby both parameters may be assessed simultaneously, each by an individual detection means.

Thereby the method may be applied in a wide variety of applications such as:

The invention allows analysis of various types of biological particles as described above and the invention is therefore particularly suited for the assessment of the number of particles in a liquid sample material in the following applications:

In particular in relation to analysis of milk samples, such as milk for dairy purposes, the invention is suitable. In milk the invention may be applied to analyse somatic cells, such as size and/or number of somatic cells in milk. Furthermore, the analysis may be carried out for bacteria in milk.

The milk may be analysed at any point of treatment of the milk, but the invention is particularly suitable for on-line or at-line analysis, wherein the milk is analysed during milking. The various operations incorporated into the device allows even persons not skilled in the art of laboratory techniques to perform valid results.

In relation to blood analysis the apparatus is suitable for all assessments on blood particles, such as the assessment of number, morphology and type of various blood cell types.

The invention may be used in laboratory or in general practice for cell counts and differential counts. Furthermore, the invention may be used by patients for example when controlling the total cell counts in connection with treatments, such as cancer treatment.

Urine samples may be analysed according to the present invention for bacteria, for example when assessment of total cell count is necessary in connection with urinary tract infections.

Also, the invention may be used when diagnosing specific cause of urinary tract infections, such as the bacteria type.

Furthermore, semen may be assessed in the present apparatus, for example the count of spermatozoa, total count as well as count of viable spermatozoa and/or dead spermatozoa may be conducted. Also the morphology of the spermatozoa may be examined by the present apparatus.

Assessment of particles in water may be conducted by the present invention, such as control of drinking water, control of waste water or water from a water purifying plant. In all applications the control may be related to the total particle count, such as bacteria count or it may more particularly be related to a monitoring process for specific bacteria, such as pathological bacteria.

With respect to assessment of bacteria the invention may also be used in connection with food or feed samples as well as petrochemical samples (eg for air-plane fuel).

Furthermore, fermentation control, i.e. control of cell growth and viable cells in fermentation tanks may be conducted by the invention. This relates to all technical fields using fermentation, such as the pharmaceutical industry for producing peptide or protein composition.

When assessing a parameter of a liquid it is preferred that the apparatus is provided with a sample compartment for housing the liquid during the assessment as discussed above.

By the present method it is also possible to assess a parameter of a solid material, such as a piece of animal tissue or cell aggregates, plant material and the like. When assessing solid material a piece of said material may be arranged in the sample plane. It is however possible to arrange the apparatus according to the invention directly on a larger part of the animal or plant assessing the part of the animal or plant excitable in the detection area.

For example the method may be applied when examining pigmented spots on the skin of a person, or when detecting bacterial or fungal growth, for example in situ on an animal or human being.

Also the method may be applied on non-organic material, such as validation of documents including notes, as a tool in technical inspections in a crime field, or when detecting failures in various constructions, such as metal constructions, where the minute failures are difficult to observe otherwise.

In the following the invention is discussed in more detail in relation to the drawings.

In FIG. 1 an apparatus 1 according to the invention is shown in schematic form. The sample is arranged in a sample compartment 2 the sample plane. Excitation light from the light sources 4a, 4b in the excitation light means 3 is exposed onto the sample through a main light path 5a, 5b.

Fluorescence signals from the sample is emitted to the detection means 6 comprising at least one detector 7. The path of the emitted signals is following an axis between the sample and the detector, the detection-sample axis 8.

The signal data are transmitted to a processor (not shown) coupled to the detecting means 6. The fluorescence signals from the sample is filtered by means of emission filter 14 and focused to the detection means 9 by means of a focusing lens 10.

The light sources 4a, 4b are arranged in a light housing 11, whereby the transmission of excitation light directly to the detection means is avoided. Furthermore excitation light filters 12a, 12b are positioned in the excitation light beam.

Figure 2:
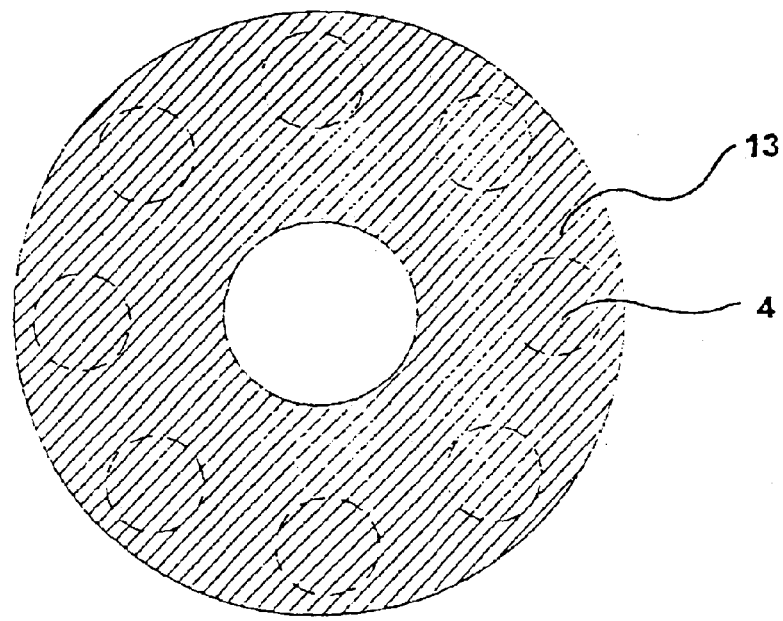
FIG. 2 shows a cross-section of the excitation light filter in a plane parallel to the sample plane.

FIG. 2 shows a cross-section of the circular supporting material 13 of he excitation light filters wherein the position of the light sources have been indicate by circles in broken lines.

Figure 3:
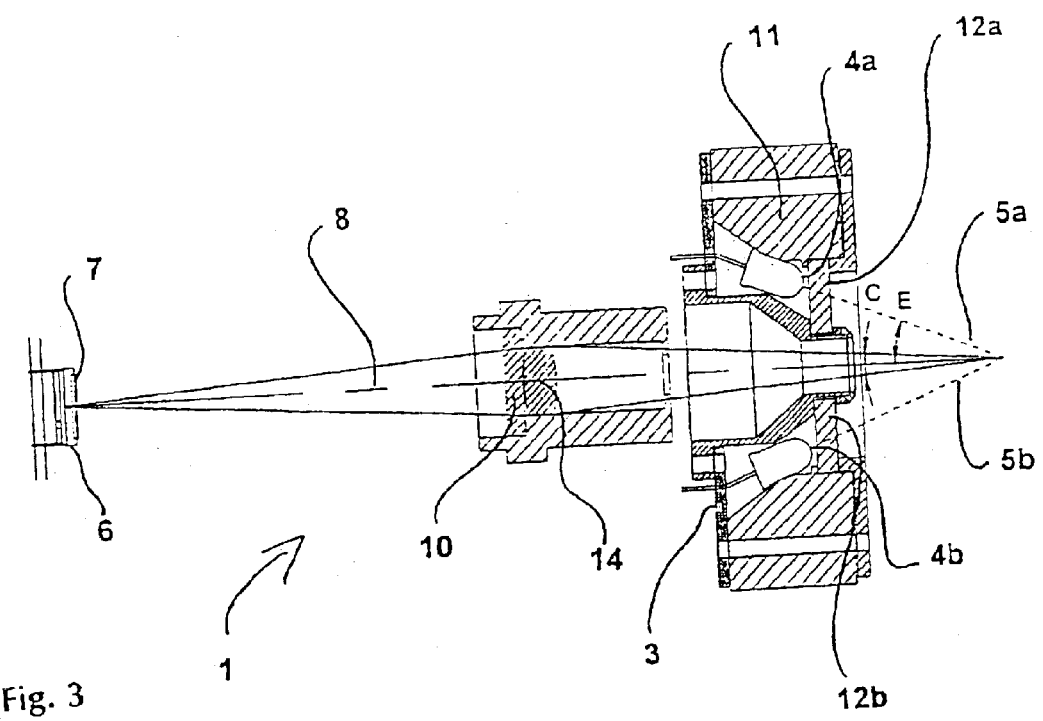
FIG. 3 shows the collection angle C and the angle E between the excitation main light path and the detection-sample axis.

In FIG. 3 the light path and signal path is shown in more detail. In the light path the main light path is shown as 5. Furthermore, the detection-sample axis is shown by broken lines 8. The collection angle of the system is denoted C shown between two arrows and the angle between the main light path and the detection-sample axis is denoted E.

Figure 4:
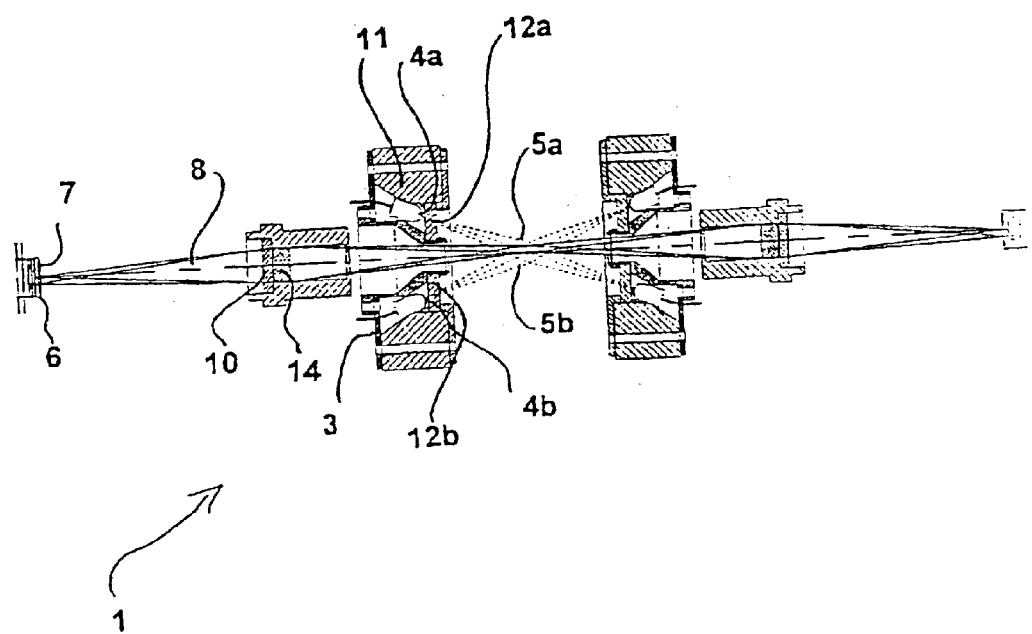
FIG. 4 shows a double-sided excitation/detection system.

In FIG. 4 a double-sided excitation/detection system 1 is shown wherein the systems on each side of the sample are identical and as described for the one-sided system of FIG. 1.

Figure 5:
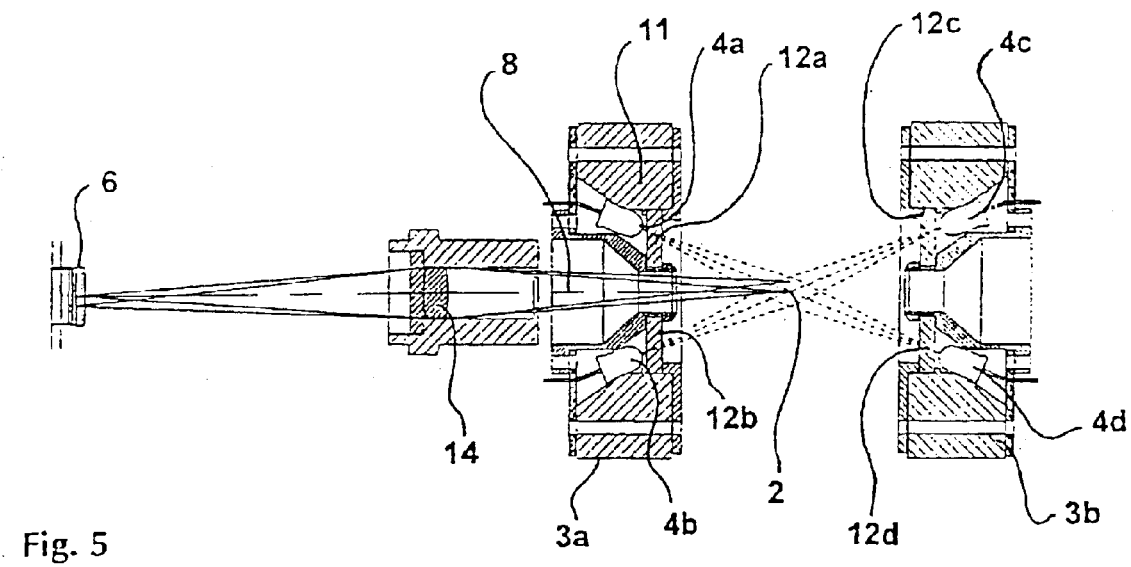
FIG. 5 shows a double-sided excitation system.

FIG. 5 shows a double-sided excitation system wherein excitation light from the light sources 4a, 4b in the first excitation light means 3a and excitation light from the light sources 4a, 4b in the second excitation light means 3b is exposed onto the sample 2 from both sides of the sample 2. As discussed above, the light sources may be identical or different depending on the information to be assessed. Furthermore, the filters used for each light source may be different or identical.

Fluorescence signals are transmitted through and reflected from the sample due to the excitation light arrangement and emitted to the detection means 6. The path of the emitted signals is following an axis between the sample and the detector, the detection-sample axis 8.

The signal data are transmitted to a processor coupled to the detecting means as described above.

Figure 6:
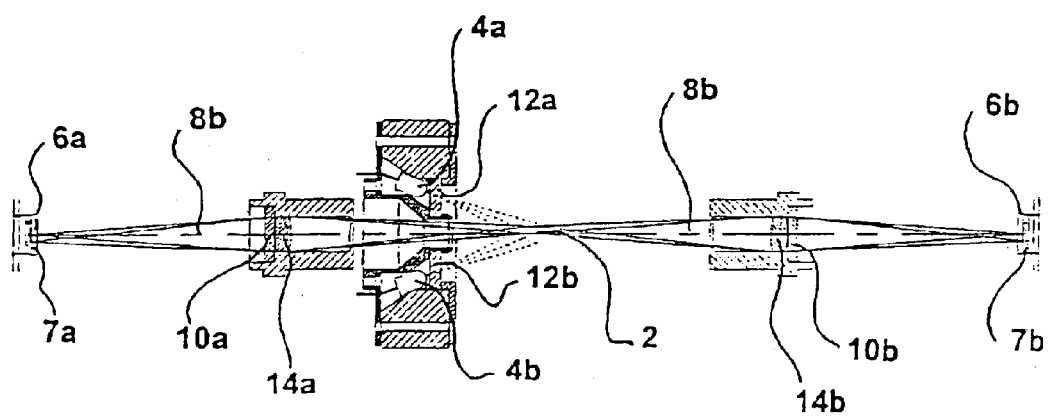
FIG. 6 shows a double-sided detection system.

FIG. 6 shows a double-sided detecting system, using a single-sided excitation system, wherein reflected fluorescence signals from the sample 2 are detected by detecting means 6a comprising detector 7a. The reflected fluorescence signals are transmitted though filter 14a and focused by lens 10a.

Furthermore, transmitted fluorescence signals from the sample 2 are detected by detecting means 6b comprising detector 7b. The reflected fluorescence signals are transmitted though filter 14b and focused by lens 10b.

Filter 14a is preferably different from filter 14b, whereby information relating to at least two different fluorescence signals is obtainable.

Also the magnification in the two detecting systems may be different, for example by lens 10a being different from lens 10b.

EXAMPLE

An Image of Cells Obtained According to the Present Invention.

An assessment of the number of somatic cells in milk is performed by detecting fluorescence signals originating from a fluorochrome bound to DNA within the cell nucleus, present in the sample compartment in a system configuration is shown in FIG. 1 and FIG. 2. The sample compartment is defined by two substantially parallel planes of transmitting material thus forming a compartment with dimensions of about 6×8×0.07 mm (height, width, depth). In the present example the sample compartment is an integrated part of a disposable cassette.

The fluorescence is generated by passing light of high energy (excitation light of wavelength 550 nm or less) through the sample compartment. The source of the excitation light is a light source, according to the present invention as illustrated in FIG. 1, comprising 8 light emitting diodes arranged as illustrated in FIG. 2. The Light emitting diodes are of the type NSPG-500S (Nichia Chemical Industries Ltd., Japan).

In order to substantially remove any component from the excitation light with wavelength above about 550 nm from reaching the sample compartment, an optical filter is inserted in the light path. This optical filter is integrated in the light source and implemented as a circular disk with a circular hole in the middle through which any emitted light from the sample compartment is allowed to pass (see FIG. 2 for further illustration). This filter of the type Ferroperm SWP550, double sided interference filter on a 2 mm substrate (Hoya, CM-500) which absorbs infra-red radiation.

The light emitted from the sample compartment is focused onto the sensors of the detection module by the use of a lens. This lens is a standard ×4 microscope objective with numerical aperture of 0.10 (one supplier is G. J. Carl Hansens Eftf., Denmark). The lens is arranged in such a way as to give an image of an object in the sample compartment on the sensors of the detection module which has approximately the same size as the original object (magnification approximately ×1).

In order to remove substantially any component from the light emitting from the sample compartment with wavelength below about 575 nm from reaching the detection module, an optical filter is inserted in the light path. This filter is of the type Schott OG590 (thickness 3 mm).

The filtered light from the sample compartment is detected by a charge couple device (CCD) of the type ICX054BL-6 (supplied by Sony).

The electrical information from the CCD is amplified and measured by an analogue to digital converter module (ADC). This information can be arranged to give an image representation of the recorded information. One such image is shown in FIG. 7.

Figure 7:
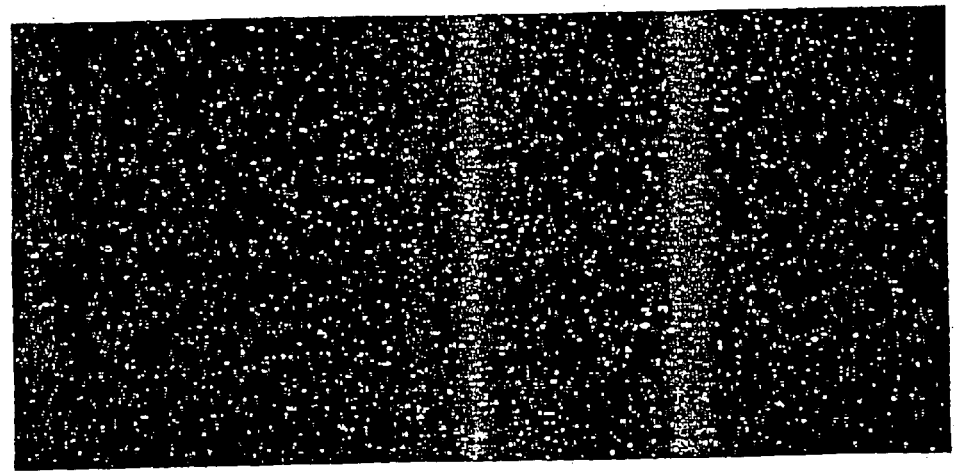
FIG. 7 shows an emission result recorded from a sample of somatic cells in milk solution.

The image in FIG. 7 is the emission result, recorded from a sample of somatic cells in milk solution containing about 1% Triton X-100 and about 30 µg/ml propidium iodide (CAS-25535-16-4) as DNA staining dye, when exited with light from a light source according to the present invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for detecting the fluorescence of a sample comprising:
   a first excitation light system including at least a first light source, the first light source having a main light path;
   a sample plane for positioning said sample;
   a detection device including at least a first detector for detecting fluorescence signals from the sample, an axis between the detection device and the sample plane being a detection-sample axis;
   a processor coupled to receive data from the detector;
   a focusing device for focusing the signals onto the detection device, said focusing device having a collection angle, an angle between the main light path of the first light source and the detection-sample axis being between the collection angle/2 and 90°, and the focusing device providing a magnification in a range of 2/1 to 1/10.

2. The apparatus according to claim 1, wherein at least the first light system is located in a first light plane parallel to the sample plane, said first light plane being between the sample plane and the detection device.

3. The apparatus according to claim 1, wherein the first light source is selected from a light emitting diode, a laser diode, a laser, a thermal light source, and a gas discharge lamp.

4. The apparatus according to claim 1, wherein an excitation light filter is inserted in the main light path from said first light source.

5. The apparatus according to claim 1, wherein said first light system includes a plurality of light sources and substantially identical filters are used for all the light sources.

6. The apparatus according to claim 1, wherein the first excitation light system includes at least two light sources, and excitation light filters for each light source are connected to each other on a supporting material.

7. The apparatus according to claim 6, wherein the supporting material has a shape selected from circular, rectangular, square, semi-circular.

8. The apparatus according to claim 1, wherein the first light source is filtered through a first filter, and a second light source is filtered through a second filter, the first filter and the second filter being different.

9. The apparatus according to claim 1, wherein a second excitation light system is located in a second light plane, said second light plane being parallel with the sample plane and located on the other side of the sample plane relative to the first light plane allowing the sample to receive excitation light from two sides.

10. The apparatus according to claim 9, wherein a filter inserted in a light path from the second light system is different from a filter inserted in the main light path of the first light source.

11. The apparatus according to claim 1, wherein the detection device includes an array of detectors.

12. The apparatus according to claim 1, wherein the detection device includes an array of charged coupled devices.

13. The apparatus according to claim 1, wherein an additional detection device is arranged so that the sample plane is positioned between the detection device and the additional detection device.

14. The apparatus according to claim 13, wherein the detection device is identical with the additional detection device.

15. The apparatus according to claim 1, wherein an emission light filter is inserted in an emission light path to at least the first detector.

16. The apparatus according to claim 15, wherein the emission light filter is selected from interference filters, coloured filters, and polarisation filters.

17. The apparatus according to claim 1, wherein the focusing device is a lens.

18. The apparatus according to claim 1, wherein a detection area of the sample is at least 0.1 mm$^2$.

19. The apparatus according to claim 1, wherein an angle between the main light path and the detection-sample is in a range between 35° and 90°.

20. The apparatus according to claim 1, wherein at least the first light system is located in a first light plane parallel to the sample plane, said first light plane being positioned at a distance from the sample plane behind the detector.

21. The apparatus according to claim 20, wherein the detector is positioned in a housing having an opening towards the sample.

22. The apparatus according to claim 1, wherein the focusing device provides a magnification in a range of 2/1 to 1/4.

23. The apparatus according to claim 22, wherein the detector is positioned in a housing having an opening towards the sample.

24. A method of assessing a parameter of a sample comprising:

arranging the sample in a sample plane;

exposing a first surface of the sample directly with excitation light from a first light system having at least a first light source;

by use of a focusing device detecting a fluorescence signal from the first surface of the sample onto a detection device including at least a first detector, an axis between the detection device and the sample plane being a detection-sample axis, said focusing device having a collection angle, an angle between an excitation main light path of the first light source and the detection-sample axis being between the collection angle/2 and 90°, and the focusing device providing a magnification in a range of 2/1 to 1/10;

processing the detected signal obtaining signal data;

correlating the signal data to the parameter to be assessed; and assessing the parameter.

25. The method according to claim 24, wherein said first light system is located in a first light plane parallel to the sample plane, said first light plane being between the sample plane and the detection device.

26. The method according to claim 24, wherein the first light source is a light emitting diode.

27. The method according to claim 24, wherein an excitation light filter is inserted in an excitation light path from said first light source.

28. The method according to claim 27, wherein the excitation light filter is arranged on a supporting material.

29. The method according to claim 24, wherein said first light system includes a plurality of light sources and substantially identical filters are used for all the light sources.

30. The method according to claim 24, wherein said first light source is filtered through a first filter, and a second light source is filtered through a second filter, the first filter and the second filter being different.

31. The method according to claim 24, further comprising exposing a second surface of the sample directly with excitation light from a second light system having at least one light source.

32. The method according to claim 31, wherein the second excitation light system is located in a second light plane, said second light plane being parallel with the sample plane and located on the other side of the sample plane relative to the first light plane allowing the sample to be exposed on two opposite surfaces.

33. The method according to claim 31, wherein a filter inserted in a light path from the second light system is different from a filter inserted in the main light path of the first light source.

34. The method according to claim 24, wherein the detection device includes an array of detection devices.

35. The method according to claim 34, wherein the detection device includes an array of charged coupled devices.

36. The method according to claim 24, wherein an additional detection device is used that is arranged so that the sample plane is positioned between the detection device and the additional detection device.

37. The method according to claim 36, wherein the detection device is identical with the additional detection device.

38. The method according to claim 24, wherein an emission light filter is inserted in an emission light path to at least the first detector.

39. The method according to claim 24, wherein a collimating lens is arranged in an emission light path to at least the first detector.

40. The method according to claim 24, wherein the sample plane is provided with a detection area.

41. The method according to claim 40, wherein said detection area is at least 0.1 mm$^2$.

42. The method according to claim 24, wherein a sample compartment is arranged in the sample plane for housing the sample.

43. The method according to claim 24, wherein the angle between the excitation main light path and the detection-sample axis is in a range between 35° and 90°.

44. The method according to claim 24, wherein at least the first light system is located in a first light plane parallel to the sample plane, said first light plane being positioned at a distance from the sample plane behind the detector.

45. The method according to claim 44, wherein the detector is positioned in a housing having an opening allowing emitted signals to reach the detector.

46. The method according to claim 24, wherein the sample is a liquid sample.

47. The method according to claim 46, wherein the fluorescence signal is related to a parameter of a particle in the sample.

48. The method according to claim 46, wherein a number of particles in said sample is assessed.

49. The method according to claim 46, wherein a morphology of a number of particles in said sample is assessed.

50. The method according to claim 49, wherein the number of particles is assessed by the detection device and the morphology of the particles is assessed by an additional detection device.

51. The method according to claim 24, wherein the sample is a part of a solid material capable of emitting a fluorescence signal.

52. The method according to claim 51, wherein the sample is tissue, parts and/or cell aggregates.

53. The method according to claim 51, wherein the sample is a document or a note.

54. The method according to claim 50, wherein the sample is a part of metal construction for detecting failure signals from the metal.

55. The method according to claim 24, wherein the excitation light is from at least two light sources, and excitation light filters for each light source are connected to each other on a supporting material.

* * * * *